United States Patent [19]

Weeks

[11] Patent Number: Plant 7,156

[45] Date of Patent: Feb. 20, 1990

[54] FLORIBUNDA ROSE PLANT NAMED SMOOTH TALK

[76] Inventor: O. L. Weeks, 12610 Central Ave., Ste. 76, Chino, Calif. 91710

[21] Appl. No.: 304,280

[22] Filed: Jan. 31, 1989

[51] Int. Cl.[4] ..... A01H 5/00

[52] U.S. Cl. ..... Plt./23

[58] Field of Search ..... Plt. 23

*Primary Examiner*—James R. Feyrer

*Attorney, Agent, or Firm*—Christie, Parker & Hale

[57] ABSTRACT

A new Floribunda rose variety of bright white coloring.

1 Drawing Sheet

SUMMARY OF THE INVENTION

The present invention relates to a new and distinct variety of rose plant of the Floribunda rose class, which was originated by my crossing as seed and pollen parents, two unnamed, unpatented seedlings of my creation. The varietal denomination of this new rose is "Smooth Talk".

Among the novel characteristics possessed by this new variety which distinguishes it from its parents and all other varieties of which I am aware are the bright white flowers of good form borne on a plant with attractive contrasting dark green foliage. The flowers which are relatively large for a Floribunda, open well, and become ruffled at maturity.

The new variety is a Floribunda rose that produces many blooms throughout the growing season and is useful for mass color effectiveness. The white coloring is bright and contrast well against attractive green foliage which covers the plant to the base. The flowers display their stamens when fully open, adding to their attractiveness.

The plant grows well, is uniformly disciplined and well contained but sufficiently spreading to fulfull landscaping purposes. The size of the flowers and the recurring blooming habit of this new cultivar makes it an eye-catching garden asset.

Asexual reproduction by budding of the new variety as performed in Kern County, Calif. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and as depicted in color as nearly true as it is reasonably possible to make the same in a color illustration of this character.

HORTICULTURAL DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart, e.g., "145B" is plate 145B of The Royal Horticultural Society Colour Chart.

Parentage: Seedling.

*Seed parent.*—Unnamed, unpatented seedling.

*Pollen parent.*—Unnamed, unpatented seedling.

Class: Floribunda.

The following observations are made of specimens grown outdoors in Kern County, Calif., during the month of October.

FLOWER

Blooming habit: Recurrent to continuous.

A. Bud:

(1) *Size.*—Medium to large.

(2) *Form.*—Long, pointed, ovoid.

(3) *Color.*—After sepals divide, color of bud is yellow green, near 145B to C becoming white to near white as sepals fall and petals begin to unfurl.

(4) *Sepals.*—Not as long as bud, slightly foliated.

(5) *Peduncle.*—Length — long for a floribundum. Aspect — straight. Strength — erect, strong. Color — yellow green, near 146B.

B. Bloom:

(1) *Size.*—Average size when fully expanded — about 3 inches.

(2) *Borne.*—Several together in medium sprays.

(3) *Form.*—High centered at first, maintains form well until open, edges of outer petals are fringed and roll under, flowers become ruffled at maturity.

(4) *Petalage.*—Number of petals under normal conditions — about 30 to 33.

(5) *Color.*—After sepals fall and as flower opens, flowers are white with cream-toned flower center where petals bunch. Outer petals have occasional dark edges.

C. Petals:

(1) *Texture.*—Thick, good substance, waxy.

(2) *Appearance.*—Inside — velvety, outside — satiny.

(3) *Form.*—Broad, fan shaped with ruffled edge.

(4) *Arrangement.*—Regularly arranged, imbricated.

(5) *Petaloids in center.*—Few.

(6) *Persistence.*—Drop off cleanly.

(7) *Fragrance.*—Slight anise.

(8) *Lasting quality.*—Moderately Long on plant and as cut flower.

REPRODUCTIVE ORGANS

A. Stamens, filaments and anthers:

(1) *Arrangement.*—Regularly arranged around styles.

(2) *Color.*—Reddish.

B. Pollen:

*Color.*—Pale yellow.

C. Styles: Medium length, thin.

D. Stigmas:

Color.—pale yellow.

E. Hips: None observed.

PLANT

A. Form: Compact, spreading.

B. Growth: Very Vigorous, uniform branching.

*Height attained.*—About 3 to 3½ feet.

C. Foliage: Compound 7 leaflets.

(1) *Size.*—Medium.

(2) *Quantity.*—Abundant.

(3) *Color.*—New foliage: Upper side — greenish bronze with reddish serrations. Under side — greenish bronze with less noticeable reddish serrations. Old foliage: Upper side — green, near 139A. Under side — near 194B.

(4) *Shape.*—Oval, pointed.

(5) *Texture.*—Leathery, semi glossy, Upper side is glossy and under side is matte.

(6) *Edge.*—Finely serrated.

(7) *Serration.*—Serrate.

(8) *Leaf stem.*—Color — near 178A to B with reddish overlay.

(9) *Stipules.*—Medium, pointed, smooth at sides.

(10) *Resistance to disease.*—Mildew — average.

D. Wood:

(1) *New wood.*—Color — near 178A to B with reddish tones. Bark — smooth but with few prickles.

(2) *Old wood.*—Color — green, near 138A. Bark — smooth.

E. Thorns:

(1) *Thorns.*—Quantity (main stalk) — few. On laterals from stalk — few. Form — oval pointed, flat base. Length — short to medium. Color — reddish green. Position — irregular.

(2) *Prickles.*—Few.

F. Winter hardiness: Average.

I claim:

1. A new and distinct variety of rose plant of the Floribunda rose class, substantially as shown and described, characterized particularly by attractive white flowers of good form.

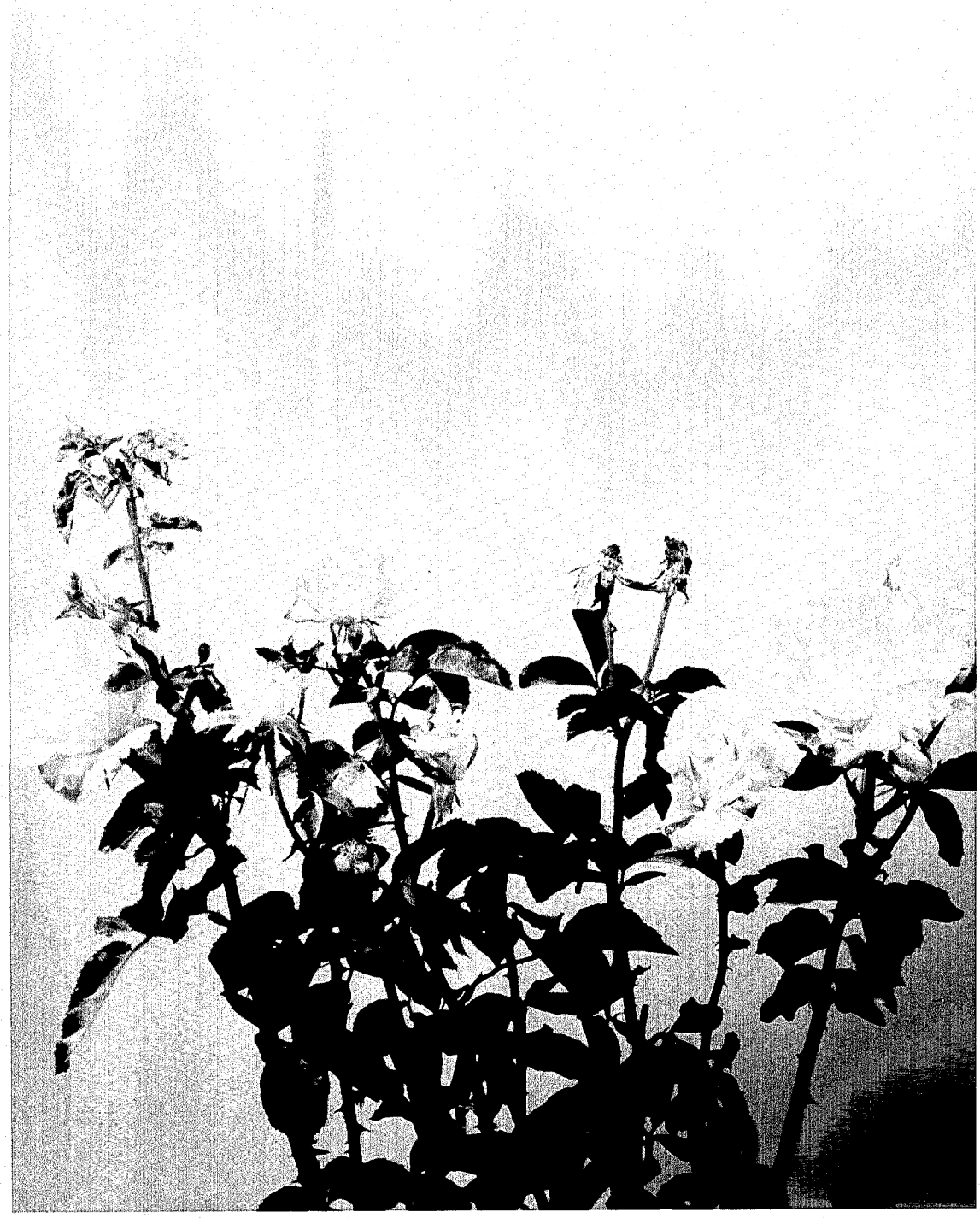

* * * * *